US012661270B2

(12) United States Patent
Liao

(10) Patent No.: US 12,661,270 B2
(45) Date of Patent: Jun. 23, 2026

(54) EARBUD

(71) Applicant: Dongguan Saienchuangke Technology Co., Ltd, Dongguan (CN)

(72) Inventor: Lixiang Liao, Dongguan (CN)

(73) Assignee: Huizhou Saienchuangke Technology Co., Ltd, Huizhou (CN)

( * ) Notice: Subject to any disclaimer, the term of this patent is extended or adjusted under 35 U.S.C. 154(b) by 642 days.

(21) Appl. No.: 18/134,049

(22) Filed: Apr. 13, 2023

(65) Prior Publication Data

US 2024/0238124 A1 Jul. 18, 2024

(30) Foreign Application Priority Data

Jan. 16, 2023 (CN) .......................... 202310076678.7

(51) Int. Cl.
A61F 11/08 (2006.01)
(52) U.S. Cl.
CPC .................................. A61F 11/085 (2022.01)
(58) Field of Classification Search
CPC ........ A61F 11/08; A61F 11/085; A61F 11/10; H04R 1/1008; H04R 1/1016
USPC ....................................... 381/380
See application file for complete search history.

(56) References Cited

U.S. PATENT DOCUMENTS

| | | | | |
|---|---|---|---|---|
| 4,133,984 A * | 1/1979 | Akiyama | ............. | H04R 25/456 |
| | | | | 381/381 |
| 4,913,165 A * | 4/1990 | Fishgoyt | ................. | A61F 11/10 |
| | | | | 128/865 |
| 9,138,353 B2 * | 9/2015 | Keady | ............. | A61M 25/10181 |
| 2012/0305329 A1 * | 12/2012 | Keady | ..................... | A61F 11/08 |
| | | | | 181/135 |

* cited by examiner

*Primary Examiner* — Camtu T Nguyen

(57) ABSTRACT

An earbud includes a connection member, a regulating valve, an earbud body and a bladder. The connection member includes opposite first and second ends and defines a through hole extending through the first end and the second end. The regulating valve defines a flow channel therein and incudes a connection end and a working end. The connection end is tightly connected to the connection member, and the working end defines a flat adjustment opening. The flow channel communicates with the through hole of the connection member. The earbud body is mounted around the regulating valve and connected tightly to the connection member or the regulating valve. The earbud body defines a first cavity therein, and the bladder is tightly connected to the connection member and defines a second cavity for containing fluid therein. The second cavity communicates with the through hole of the connection member.

18 Claims, 17 Drawing Sheets

A-A

B-B

C–C

D-D

E-E

EARBUD

CROSS-REFERENCE TO RELATED APPLICATIONS

The present application claims priority of Chinese Patent Application No. 202310076678.7, filed on Jan. 16, 2023, the entire contents of which are hereby incorporated by reference.

TECHNICAL FIELD

The present application relates to the field of earbuds, and in particular to an earbud that is stable and comfortable to wear and is waterproof and anti-noise.

DESCRIPTION OF THE PRIOR ART

Earbuds are generally made of silicone gel, low-pressure foam material or high-elastic polyester material. When inserted into the ear canal, the earbud is tightly contact with the external ear canal to isolate sound from entering the middle and inner ear for sound insulation purpose, thereby protecting person's hearing.

However, conventional earbuds are relatively hard and there is a significant swelling sensation when they are worn. Further, conventional earbuds are difficult to adjust their size, which makes them easy to drop, and the size of the ear canal of each person is different from that of other persons, inconvenient adjustment of the earbuds may lead to difficulty in fixing of the earbuds or swelling of the ears.

SUMMARY OF THE DISCLOSURE

Based on this, it is necessary to provide an ear but that address the problem existing in the prior art. Against the shortcomings of the prior art, an object of the present application is to provide a noise-canceling earbud that may be worn stably and comfortably for a long time, to address the problem that the earbud is easy to drop, and inconvenient adjustment of the earbuds may lead to difficulty in fixing of the earbuds or swelling of the ears since the size of the ear canal of each person is different from that of other persons.

Provided is an earbud including a connection member, a regulating valve, an earbud body and a bladder. The connection member includes opposite first and second ends and defines a through hole extending through the first end and the second end. The regulating valve defines a flow channel therein and includes a connection end and a working end. The connection end is tightly connected to the connection member, and the working end defines a flat adjustment opening. The flow channel communicates with the through hole of the connection member. The earbud body is mounted around the regulating valve and connected tightly to the connection member or the regulating valve. The earbud body defines a first cavity therein, and the bladder is tightly connected to the connection member and defines a second cavity for containing fluid therein. The second cavity communicates with the through hole of the connection member. When the earbud is in a natural state, the adjustment opening is in a closed state to prevent the first cavity from communicating with the flow channel; when the bladder is compressed, the fluid flows from the second cavity, passes through the through hole and the flow channel, pushes open the adjustment opening and enters the first cavity to make the earbud body expand; when the fluid stops to enter the first cavity via the adjustment opening, the adjustment opening reverts to the closed state to prevent backflow of the fluid from the first cavity into the flow channel; and when the working end of the regulating valve is compressed to open the adjustment opening, the fluid flows back from the first cavity, passes through the adjustment opening, the flow channel and the through hole and returns to the bladder, so as to make the earbud body to contract to its natural state.

In one of the embodiments, the connection end of the regulating valve is tightly connected to the first end of the connection member; and the bladder is tightly connected to the second end of the connection member.

In one of the embodiments, the connection member further includes a main rod, the first end and the second end are provided at two ends of the main rod, respectively; and a size of each of the first end and second end is larger than the size of the main rod.

In one of the embodiments, each of the main rod, the first end and the second end is cylindrical-shaped, and a diameter of each of the first end and the second end is larger than the diameter of the main rod.

In one of the embodiments, the regulating valve is an elastic gel member, the flow channel of the regulating valve forms a connection hole at the connection end; and the size of the connection hole in the natural state is smaller than size of the first end.

In one of the embodiments, an end surface of the working end is elongated, and the adjustment opening is provided on the end surface of the working end and is elongated and linear-shaped in the natural state.

In one of the embodiments, an outer side of the working end is provided with inclined pressure surfaces at positions corresponding to two sides of the adjustment opening.

In one of the embodiments, the earbud body is an elastic gel member.

In one of the embodiments, an end of the earbud body facing the regulating valve defines a mounting opening, a size of the mounting opening in the natural state is smaller than the size of the regulating valve, and the earbud body is tightly mounted around the entire regulating valve and the first end of the connecting member after expanding of the mounting opening.

In one of the embodiments, the bladder is an elastic gel member and is connected to the second end by snap-fit.

In one of the embodiments, the connection member further includes a main rod connecting the first end with second end, the earbud body is tightly mounted around the main rod, and the bladder is mounted around a portion of the earbud body mounted around the main rod.

In one of the embodiments, a snap member is mounted around the earbud body and the bladder, the snap member is configured for fixing the regulating valve, the earbud body and the bladder to the connection member.

In one of the embodiments, the bladder is provided with a fixed end facing the connection member, a side wall of the fixed end defines an arcuate groove; and the snap member is provided with a protrusion that is engaged into the arcuate groove.

In one of the embodiments, the snap member includes a first snap-fit part and a second snap-fit part which are matched with each other, the first snap-fit part is semi-annular-shaped and the second snap-fit part is semi-annular-shaped, and the first snap-fit part and the second snap-fit part cooperate to form a ring-shaped configuration.

In one of the embodiments, the first snap-fit part is provided with a stud at a surface thereof facing the second snap-fit part, and the second snap-fit is correspondingly provided with a recess to accommodate the stud.

In one of the embodiments, the bladder includes a fixed end facing the connection member, a side wall of the fixed end is provided with arcuate grooves, the first snap-fit part is provided with a first arcuate bar and the second snap-fit part is provided with a second arcuate bar, each of the first arcuate bar and the second arcuate bar is engaged into one corresponding arcuate groove; the number of the arcuate grooves is two, and the arcuate grooves are spaced apart from each other.

The beneficial effects of the present application are as follows:

1. the earbud of the present application can be repeatedly cleaned and used; 2. the earbud expands from inside to outside and has better sealing effect; 3. double silicone gel layers of the earbud provide better sound insulation; 4. the size of the earbud may be adjusted according to the needs, the earbud has strong adaptability, strong fastness and is not easy to disengage.

DESCRIPTION OF EMBODIMENTS

Figure 1:
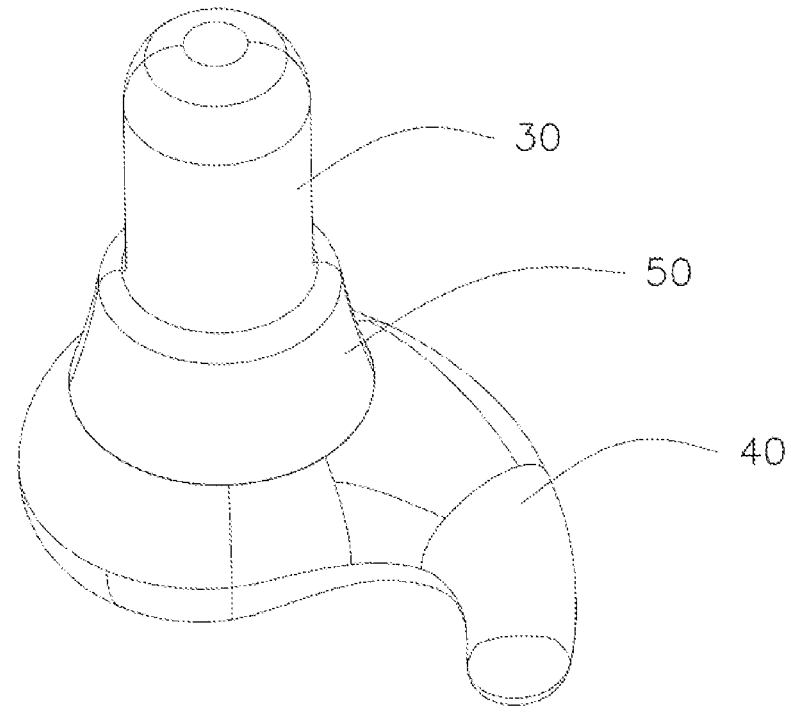
FIG. 1 is a schematic view of an earbud of a first embodiment of the application, wherein the earbud is in a natural state.
Figure 2:
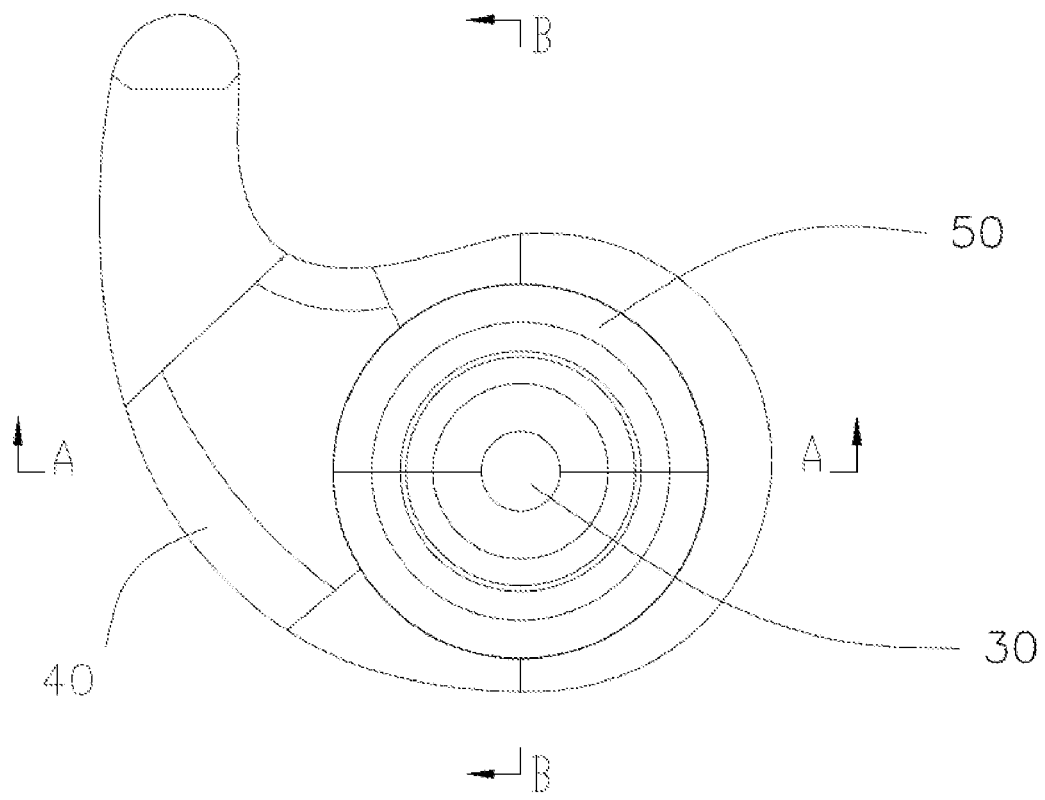
FIG. 2 is a top view of the earbud of FIG. 1.
Figure 3:
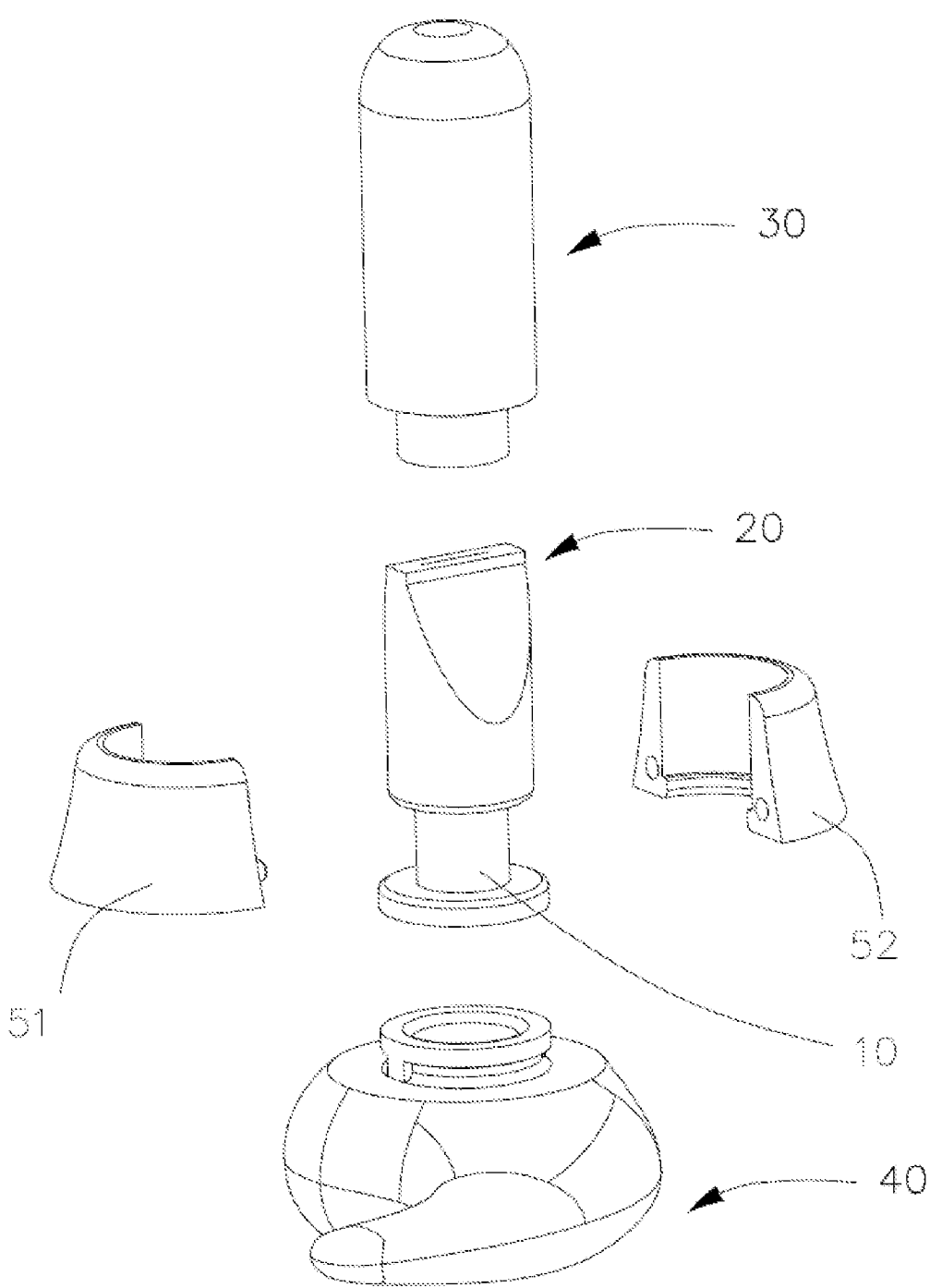
FIG. 3 is a schematic, partially exploded view of the earbud of FIG. 1.
Figure 4:
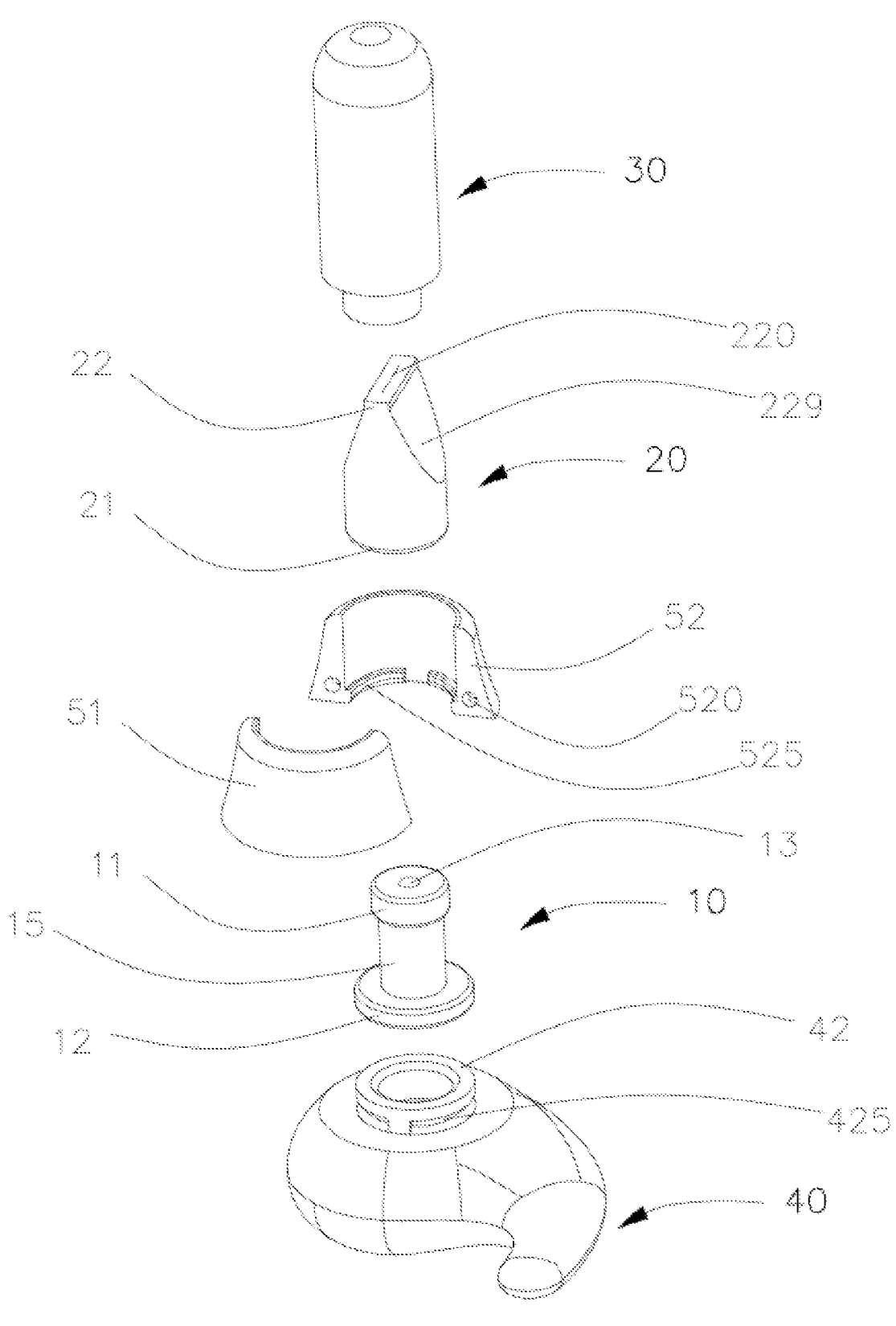
FIG. 4 is a schematic, exploded view of the earbud of FIG. 1.
Figure 5:
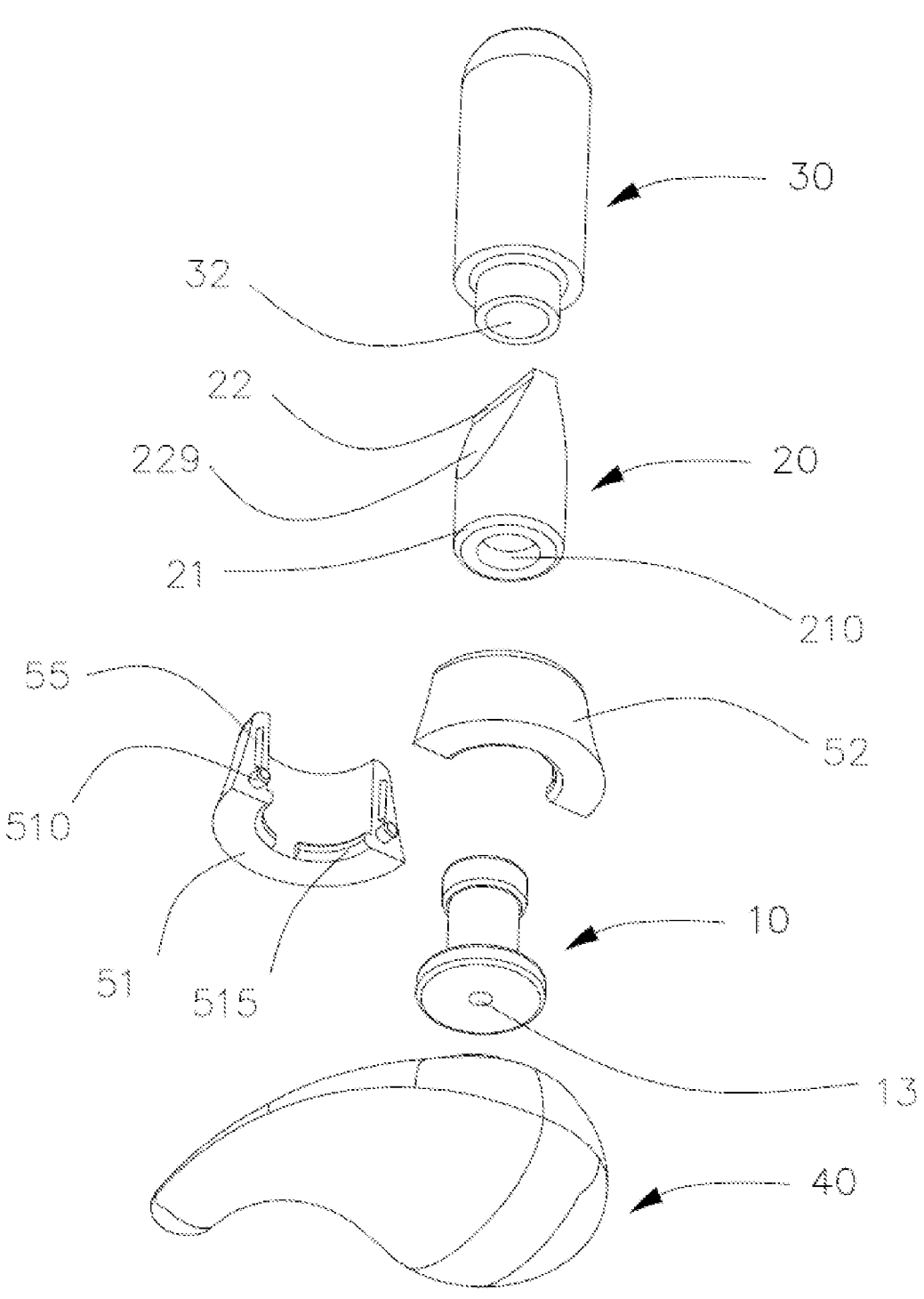
FIG. 5 is a schematic view of the earbud of FIG. 4 from another aspect.
Figure 6:
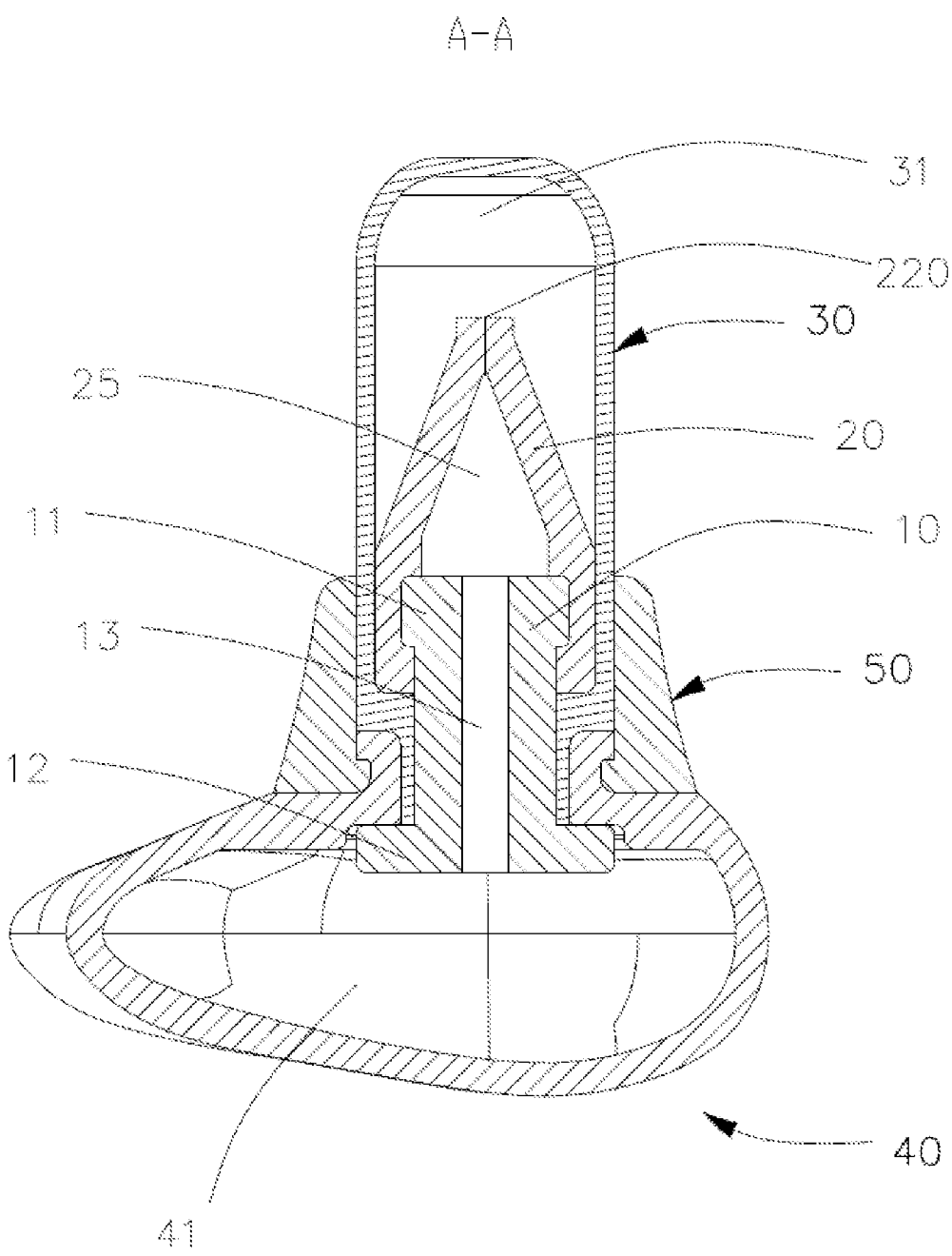
FIG. 6 is a cross-sectional view of the earbud of FIG. 2 taken along line A-A.
Figure 7:
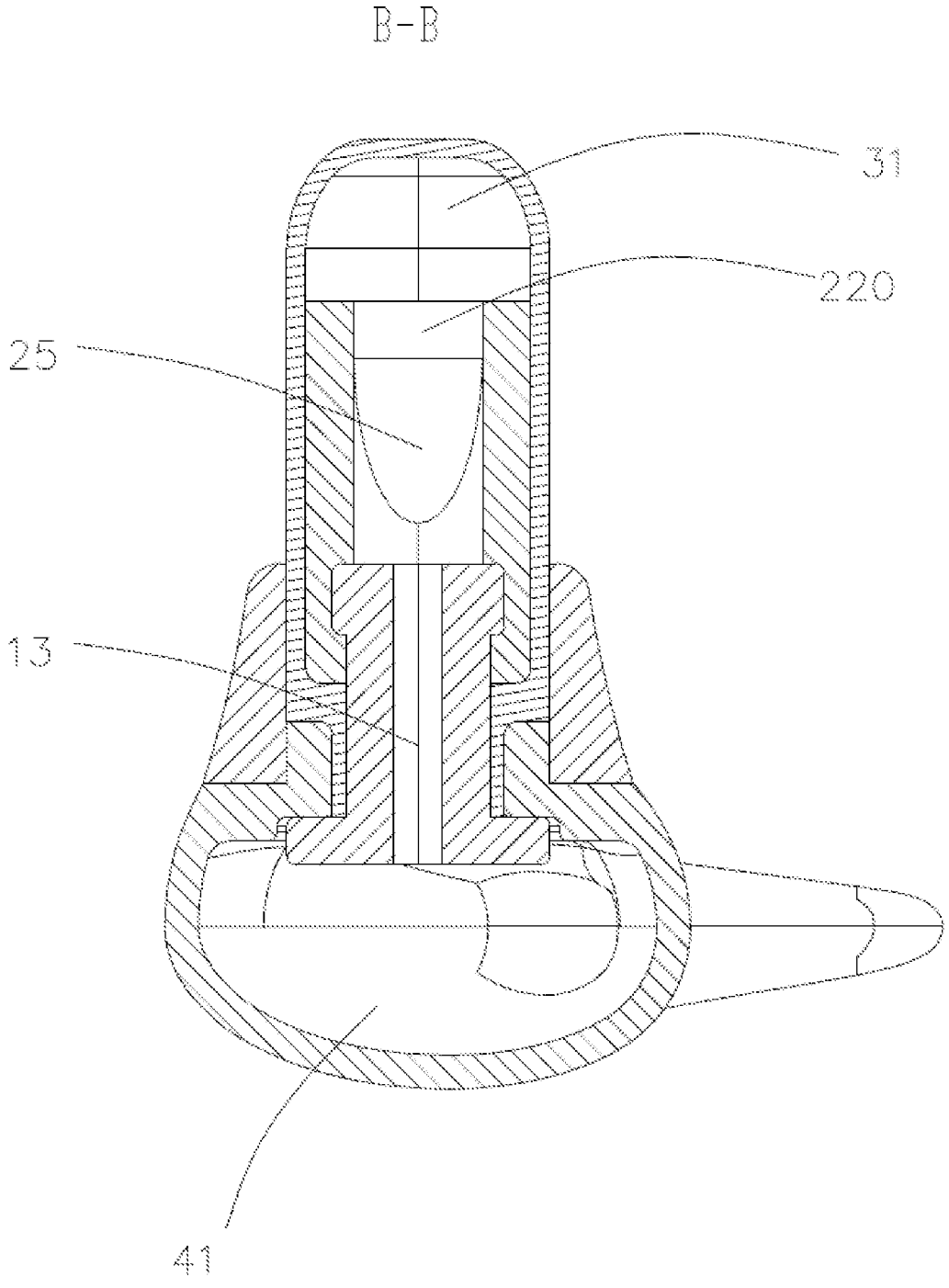
FIG. 7 is a cross-sectional view of the earbud of FIG. 2 taken along line B-B.
Figure 8:
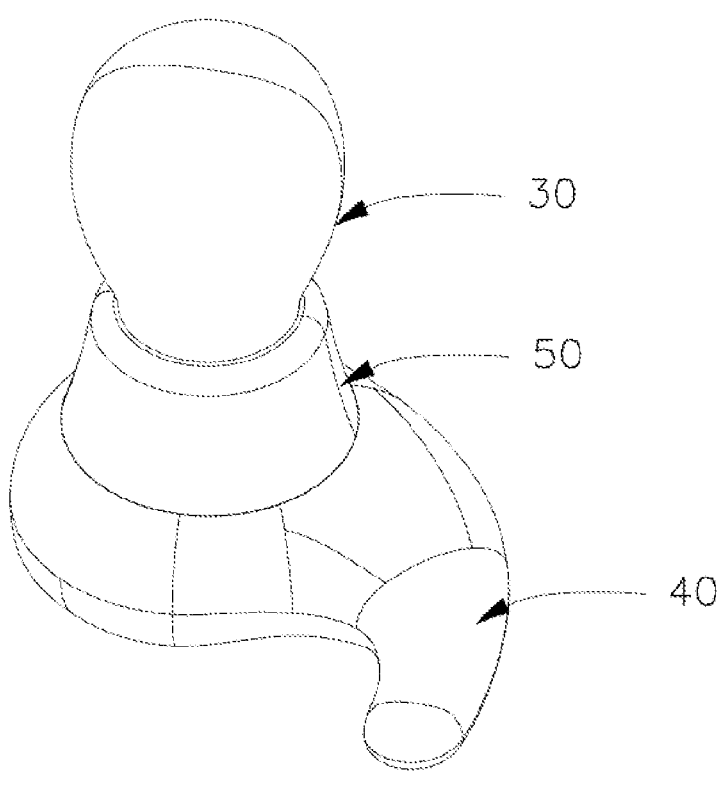
FIG. 8 is a schematic view of the earbud of FIG. 1 in a use state, wherein an earbud body thereof is in an expanded state.
Figure 9:
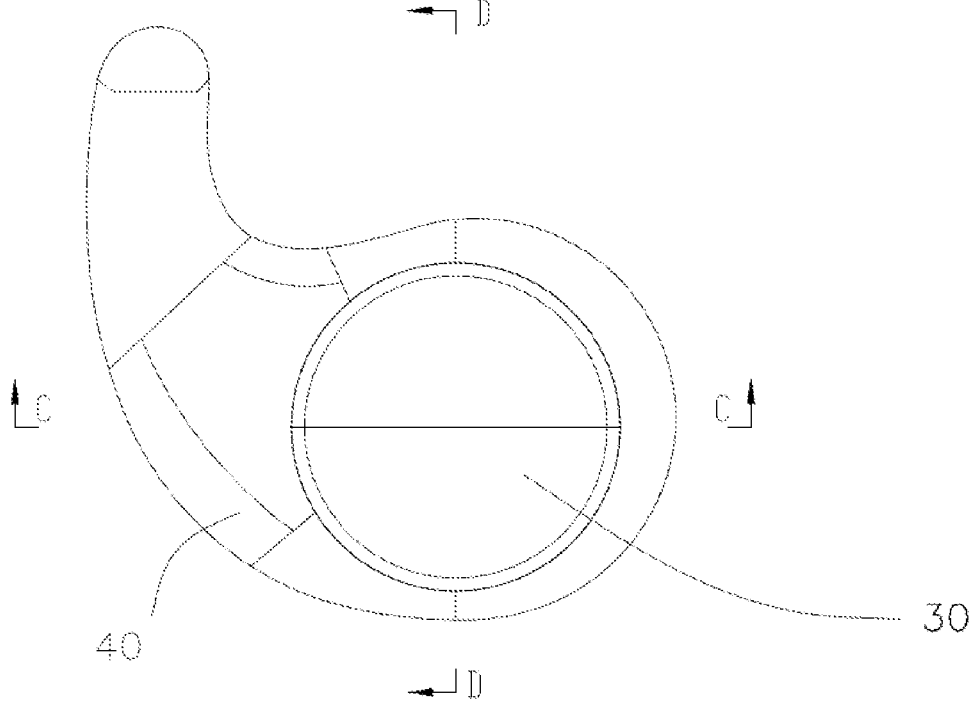
FIG. 9 is a top view of the earbud of FIG. 8.
Figure 10:
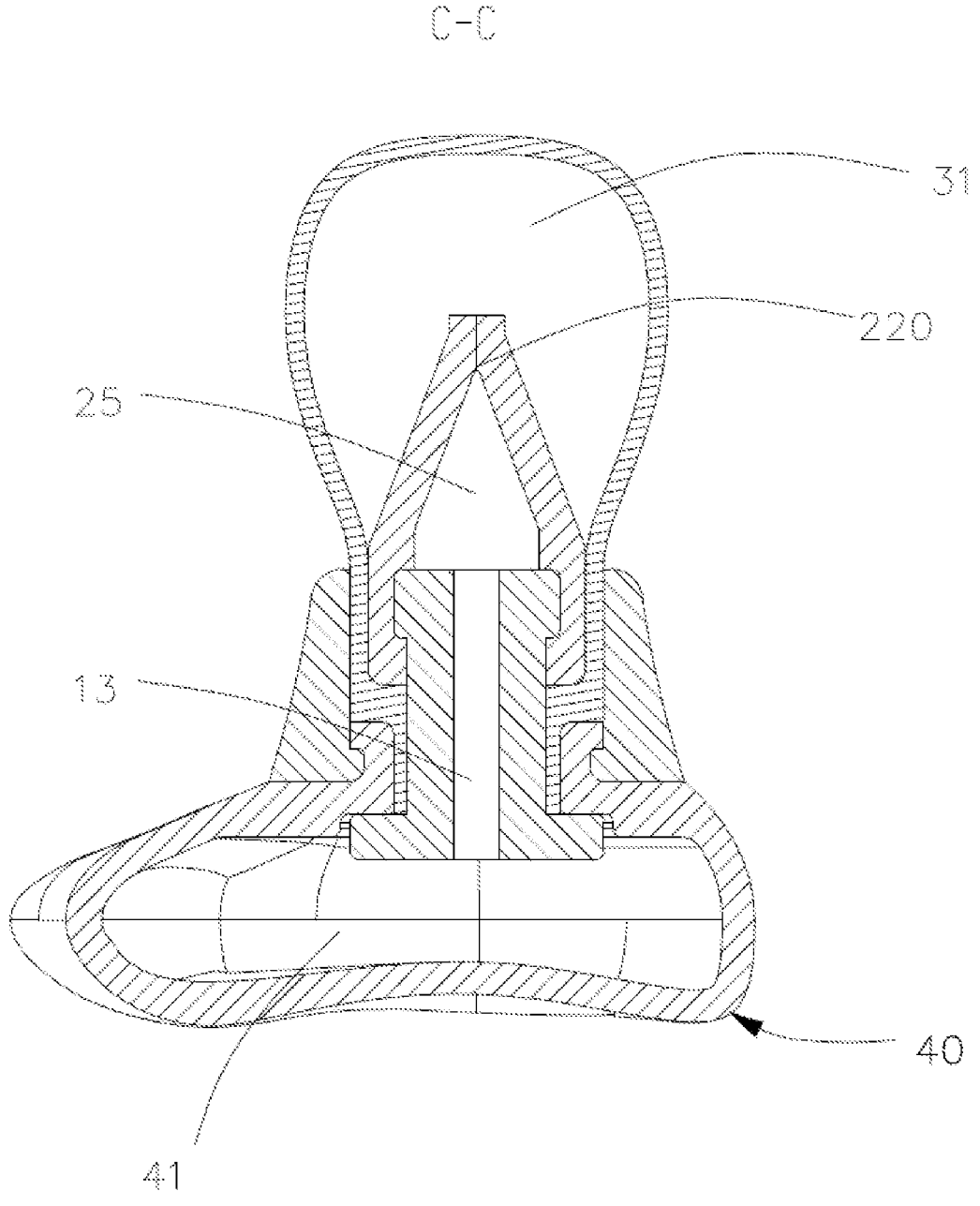
FIG. 10 is a cross-sectional view of the earbud of FIG. 9 taken along line C-C.
Figure 11:
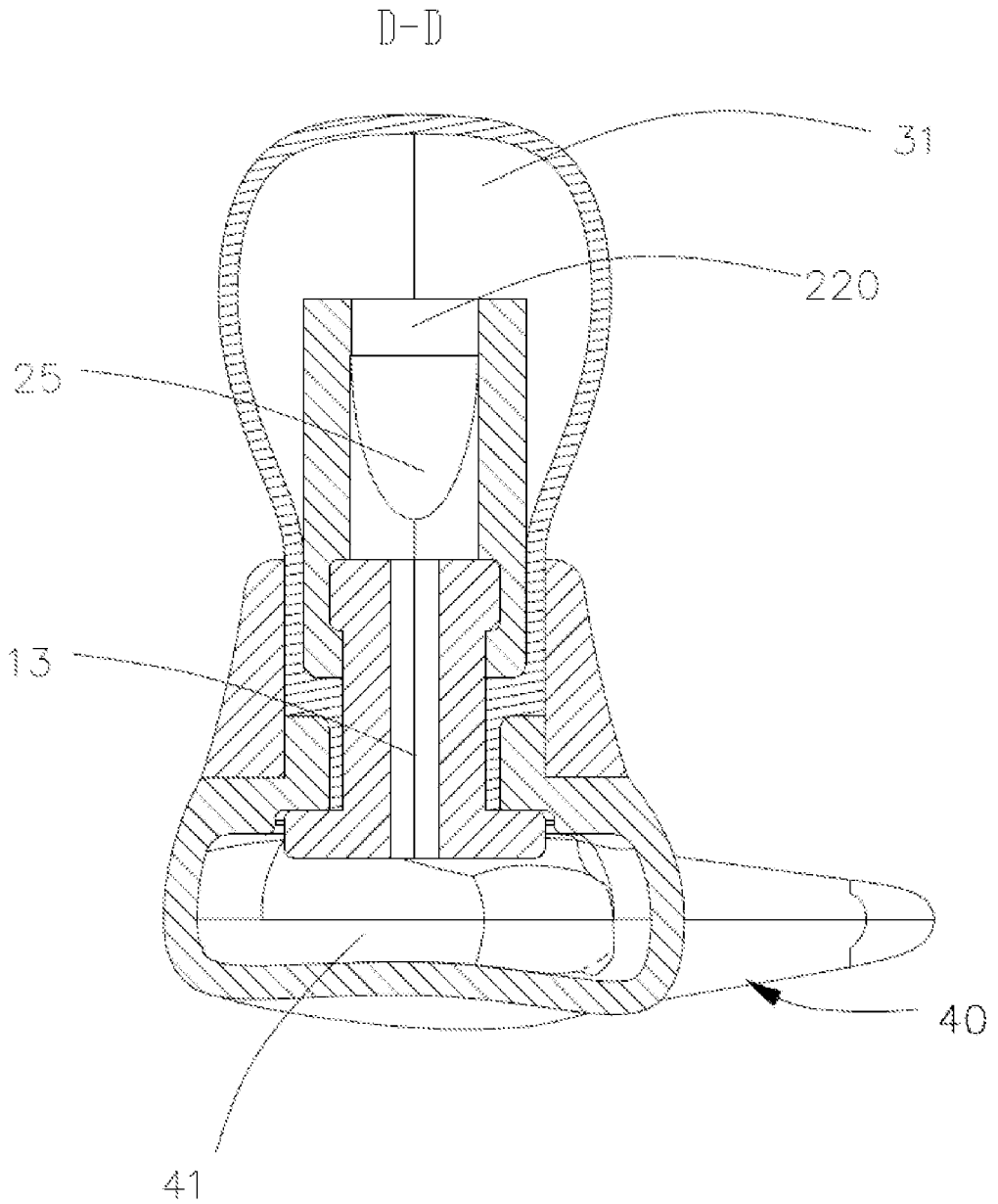
FIG. 11 is a cross-sectional view of the earbud of FIG. 9 taken along line D-D.
Figure 12:
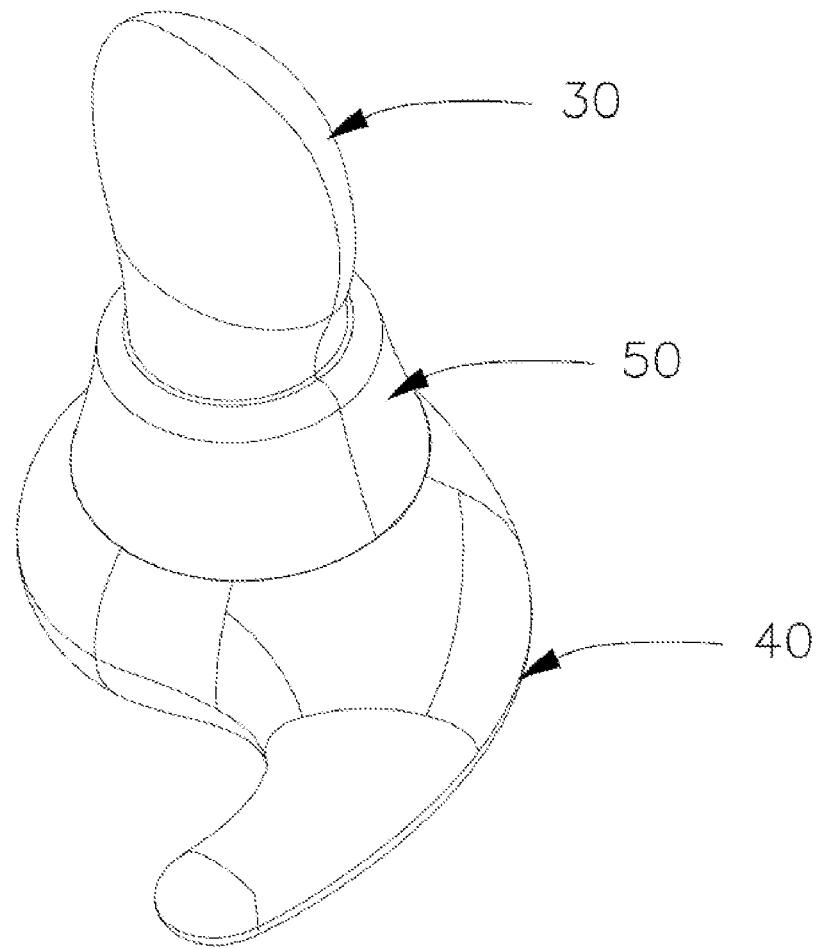
FIG. 12 is a schematic view of the earbud of FIG. 1 in a recovery state, wherein the earbud body is in a state of being pinched.
Figure 13:
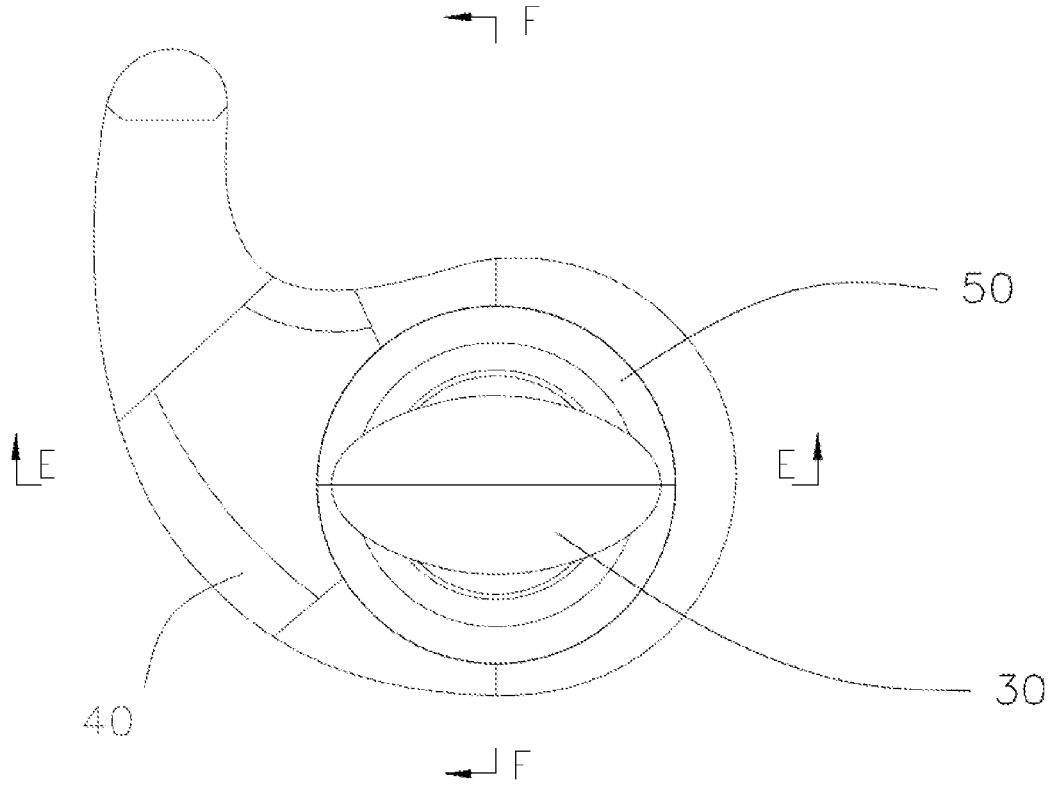
FIG. 13 is a top view of the earbud of FIG. 12.
Figure 14:
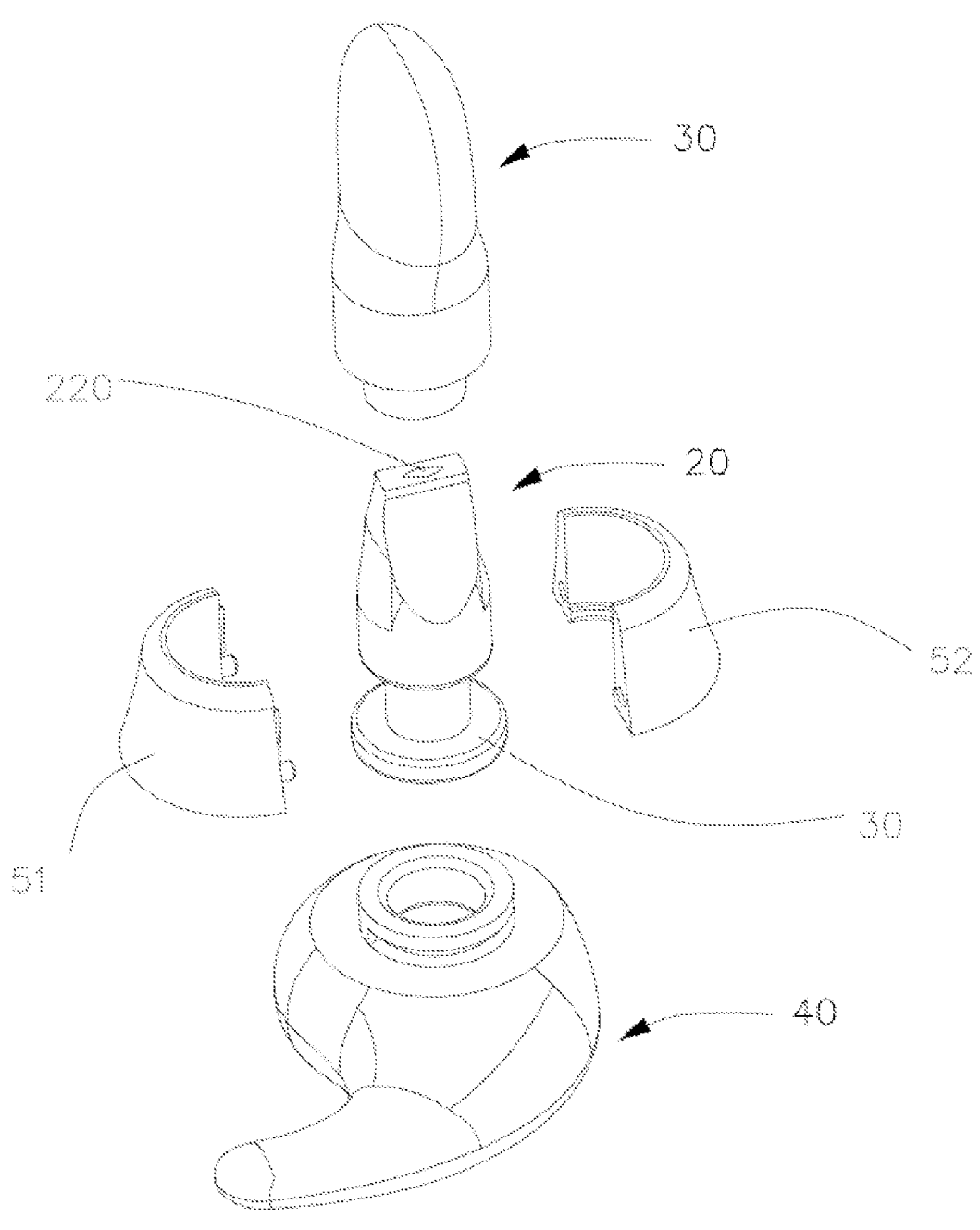
FIG. 14 is a schematic, exploded view of the earbud of FIG. 12.
Figure 15:
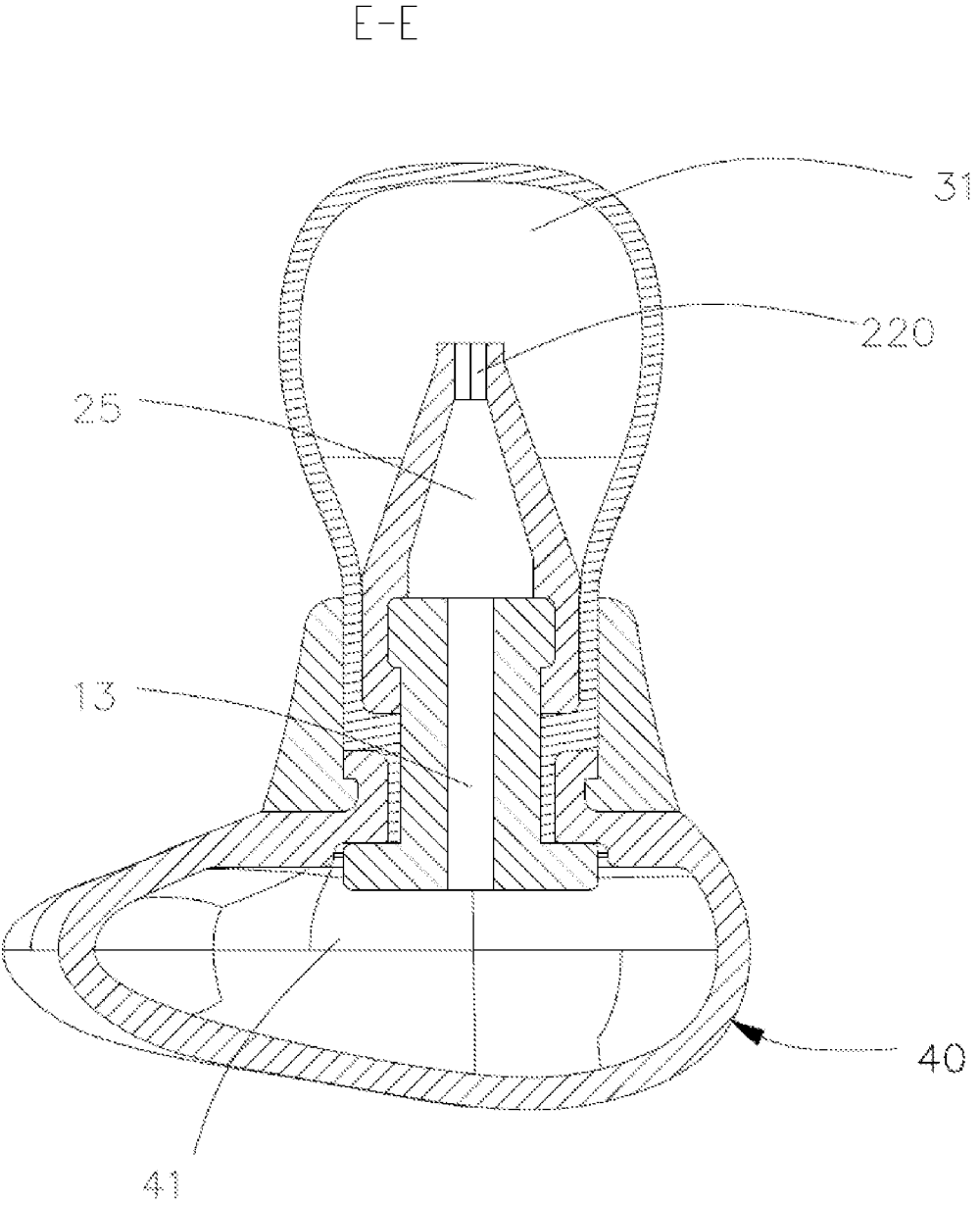
FIG. 15 is a cross-sectional view of the earbud of FIG. 13 taken along line E-E.
Figure 16:
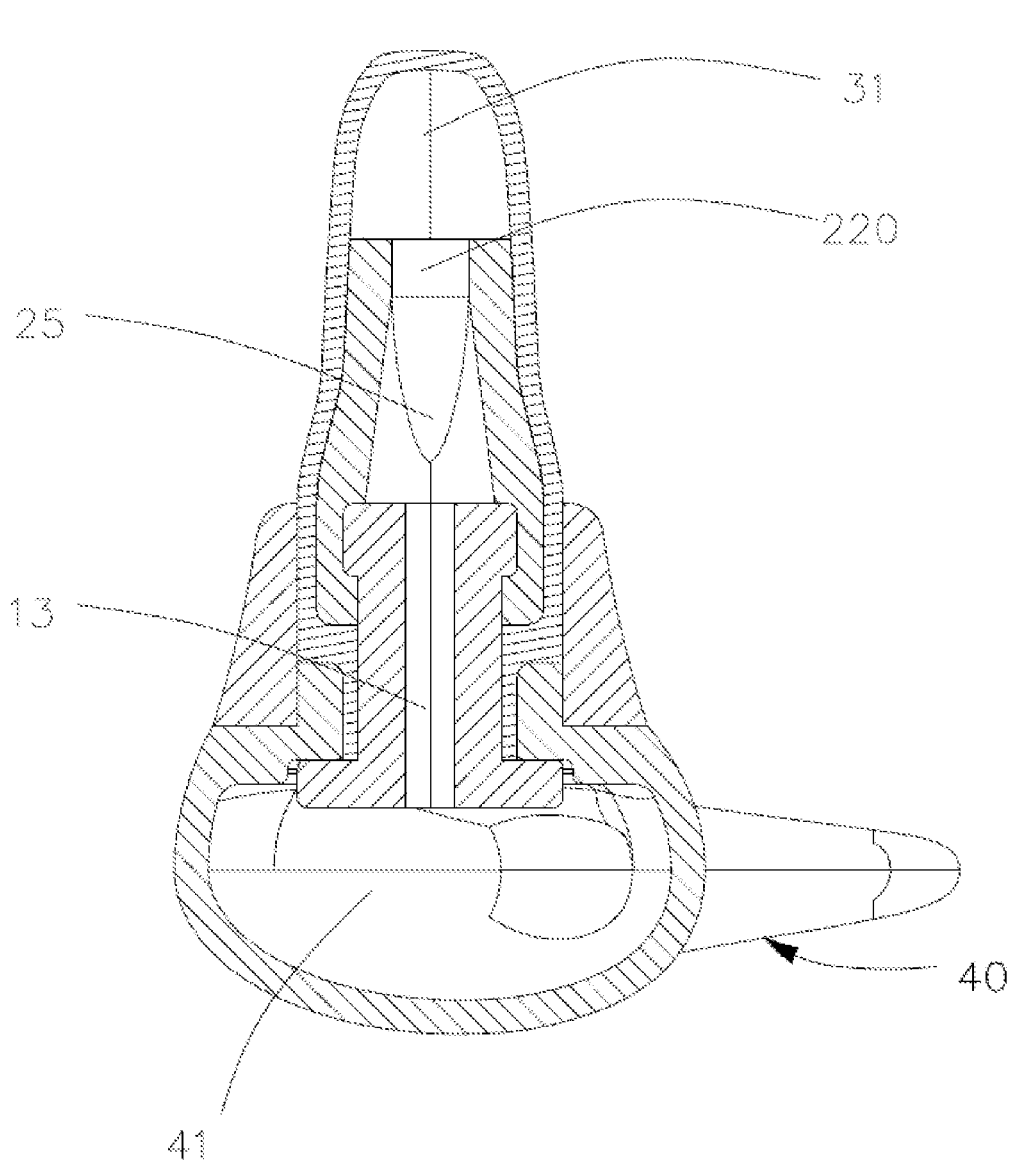
FIG. 16 is a cross-sectional view of the earbud of FIG. 13 taken along line F-F.

To facilitate an understanding of the present application, a more comprehensive description of the present application will be given below. This application may, however, be embodied in many different forms and is not limited to the embodiments described herein. Rather, these embodiments are provided for the purpose of giving a more thorough and comprehensive understanding of the disclosure of the application.

Unless defined otherwise, all technical and scientific terms used herein have the same meanings as generally understood by a skilled person in the technical field belonging to the application. The terms used in the description of the application herein is for the purpose of describing particular embodiments only and is not intended to limit the application.

Referring to FIGS. 1-16, an earbud according to a first embodiment of the present application is shown. The earbud is used to be inserted into the ear canal of the user, forming a seal therebetween to reduce noise interference, prevent water from entering the ear, and etc.

The earbud includes a connection member 10, a regulating valve 20, an earbud body 30 and a bladder 40. The connection member 10 includes opposite first end 11 and second end 12, and defines a through hole 13 therein. The through hole extends through the first end 11 and the second end 12. The regulating valve 20 is tightly connected to the first end 11 of the connection member 10. The earbud body 30 is mounted around the regulating valve 20, and connected tightly to the connecting member 10 or to the regulating valve 20. The bladder 40 is tightly connected to the second end 12 of the connection member 10. The regulating valve 20 includes a connection end 21 and a working end 22, the connection end 21 is tightly connected to the first end 11 of the connection member 10, and the working end 22 is provided with a flat adjustment opening 220. The regulating valve 20 defines a flow channel 25 communicating with the through hole 13 therein. The earbud body 30 includes a first cavity 31. The bladder 40 defines a second cavity 41 for communicating fluid therein, and the second cavity 41 communicates with the through hole 13.

When the earbud is in a natural state, the adjustment opening 220 is in a closed state to prevent the first cavity 31 from communicating with the flow channel 25. When the bladder 40 is compressed, the fluid flows from the second cavity 41, passes through the through hole 13 and the flow channel 25, and then pushes open the adjustment opening 220 and thus enters the first cavity 31 to cause expansion of the earbud body 30. After the fluid stops to enter the first cavity 31 via the adjustment opening 220, the adjustment opening 220 reverts to the closed state to prevent backflow of the fluid from the first cavity 31 into the flow channel 25. When the working end 22 of the regulating valve 20 is compressed to open the adjustment opening 220, the adjustment opening 220 communicates with the first cavity 31 and the flow channel 25, such that the fluid flows back from the first cavity 31, passes through the adjustment opening 220, the flow channel 25 and the through hole 13 and returns to the second cavity 41 of the bladder 40, so as to make the earbud body 30 to contract to the natural state.

In this embodiment, "connected tightly" refers to a sealing connection, i.e., a connection that has good tightness, without problems such as air leakage or liquid leakage.

In this embodiment, the fluid is gas, and more particularly may be air. In other embodiments, the fluid may be liquid, or a medium such as a gas-liquid mixture. In addition, in the natural state, both the earbud body 30 and the bladder 40 may be filled with fluid, which does not limit that the fluid is only stored in the bladder 40. As long as the size of the earbud body 30 can be adjusted by adjusting a flow of the fluid from the bladder 40 to the earbud body 30 or from the earbud body 30 to the bladder 40.

Referring to FIGS. 1-7, which are schematic illustrations of the earbud in an initial natural state. The connection member 10 further includes a main rod 15, the first end 11 and the second end 12 are provided at two ends of the the main rod 15, respectively. Each of the first end 11 and the second end 12 has a size larger than the size of the main rod 15. In this embodiment, each of the first end 11 and the second end 12 extends outwardly and radially from an outer periphery of one corresponding end of the main rod 15, to facilitate the connection of the regulating valve 20 and the earbud body 30 to the first end 11, and the connection of the bladder 40 to the second end 12. In particular, the main rod 15, the first end 11 and the second end 12 each are cylindrical shaped, wherein the diameter of each of the first end 11 and the second end 12 is larger than the diameter of the main rod 15, thereby forming a shape with two large ends and a small middle. In the this embodiment, the diameter of the second end 12 is larger than the diameter of the first end 11. The through hole 13 extends through the main rod 15, the first end 11 and the second end 12, thereby respectively forming a port on each of the first end 11 and the second end 12. In this embodiment, the connection member 10 is a plastic member, which plays the role of fluid guidance and support stability. More specifically, the connection member 10 may be selected from ABS (Acrylonitrile Butadiene Styrene) plastic members or PC (Polycarbonate) plastic members.

The regulating valve 20 is an elastic gel member, and in particular, in this embodiment, is a silicone gel member. The flow channel 25 of the regulating valve 20 forms a connection hole 210 at the connection end 21, and the connection hole 210 can be elastically expanded and contracted. In the natural state, the size of the connection hole 210 is smaller than the size of the first end 11. During assembly, the connection hole 210 of the connection end 21 is enlarged and then mounted around the first end 11 of the connection member 10, so that the connection end 21 of the regulating valve 20 is connected tightly to the first end 11 of the connection member 10 to intercommunicate the flow channel 25 with the through hole 13 and a hermeticity therebetween is guaranteed. At the same time, the tight connection between the connection end 21 and the first end 11 further prevents the regulating valve 20 from easily falling off the connection member 10. It will be appreciated that in other embodiments, the connection end 21 of the regulating valve 20 and the first end 11 of the connection member 10 may be connected together by gluing, injection molding or the like, in addition to the elastic snap connection of the present embodiment, as long as the tightness and airtightness are guaranteed.

The working end 22 of the regulating valve 20 is duckbill shaped. The working principle of the regulating valve 20 is as follows: when the regulating valve 20 without an internal pressure, an outlet of the duckbill shaped working end 22 is closed under its own elastic action; as the internal pressure gradually increases, the outlet of the duckbill shaped working end 22 gradually expands to keep the fluid being exhausted at a high flow rate. More specifically, an outer side of the working end 22 is provided with two inclined pressure surfaces 229 at positions corresponding to two sides of the adjustment opening 220. The adjustment opening 220 is in a contracted and closed state, either in its natural state or in the expanded state of the earbud body 30, due to the elasticity of the regulating valve 20 and the force of the fluid on the pressure surfaces 229. In particular, an end surface of the working end 22 is elongated, and the adjustment opening 220 is provided on the end surface of the working end 22. The adjustment opening 220 is elongated and linear-shaped in the natural state, i.e., is substantially a slit opening. When the fluid within the flow channel 25 generates a pressure and impinges on the adjustment opening 220, the adjustment opening 220 is pushed open for flowing of the fluid out therethrough when an internal pressure on the adjustment opening 220 is greater than the pressure of the external pressure surfaces 229. Once the fluid pressure in the flow channel 25 is disappeared, the adjustment opening 220 is contracted and closed again by the force of the pressure surfaces 229 and its elastic force, thereby preventing backflow of the fluid from the earbud body 30 through the adjustment opening 220 into the flow channel 25. When the working end 22 of the regulating valve 20 is pinched by an external force (directly on the surface of the earbud body 30), the adjustment opening 220 is opened by forcefully compressing opposite sides of the adjustment opening 220, thereby enabling the fluid to flow from the earbud body 30 into the flow channel 25 through the adjustment opening 220. Understandably, the regulating valve 20 may also be referred to as a duckbill valve, a check valve, or the like.

The earbud body 30 is used for insertion into the ear canal, attaching to the ear canal closely after expansion to insulate sound from entering the middle ear and the inner ear, or to play a waterproof role. The earbud body 30 is an elastic gel member, and in particular, in this embodiment, is a silicone gel member. The earbud body 30 is in a shape of capsule or bullet shell, one end of the earbud body 30 facing the regulating valve 20 is provided with a mounting opening 32 for tightly connecting the connection member 10, and the mounting opening 32 communicates with the first cavity 31. In particular, the earbud body 30 has the function of elastic stretching. Further, the size of the mounting opening 32 in the natural state is smaller than the size of the regulating valve 20, and the earbud body 30 is tightly mounted around the entire regulating valve 20 and the first end 11 of the connection member 10 after expansion of the mounting opening 32 by an external force. In particular, the earbud body 30 tightly surrounds the main rod 15 of the connection member 10 through its elasticity. At the same time, a side wall of the earbud body 30 is tightly constricted against the connection end 21 of the regulating valve 20, thereby pressing the connection end 21 of the regulating valve 20 against the first end 11 of the connection member 10 and a part of the main rod 15, such that the connection end 21 of the regulating valve 20 is more fixedly mounted onto the first end 11 of the connection member 10.

The bladder 40 is connected to the second end 12 of the connection member 10 for supplying the fluid to the earbud body 30 through the connection member 10 and the regulating valve 20. In this embodiment, the bladder 40 is teardrop shaped for easy pinching by user's hand. The bladder 40 has a large volume so that the second cavity 41 has a large enough volume to accommodate the fluid. The bladder 40 is an elastic gel member, and in particular, in this embodiment, the bladder 40 is made of silicone gel. One end of the bladder 40 facing the connection member 10 acts as a fixed end 42, and the fixed end 42 defines a fixed hole 420 in communication with the second cavity 41. In this embodiment, the size of fixed hole 420 is smaller than the size of the second end 12 of the connection member 10, the fixed hole 420 is elastically expanded and then the bladder 40 is mounted around the second end 12 and attach to the main rod 15 of the connection member 10 tightly, thereby snapping the connection member 10 by the elastic contracting force of the bladder 40. In this embodiment, for a better match, the earbud body 30 is tightly mounted around the main rod 15 of the connection member 10 and the fixed end 42 is then mounted around a portion of the earbud body 30 that is mounted around the main rod 15 (i.e. a portion of the earbud body 30 is clamped between an outer wall of the main rod 15 and the fixed end 42 of the bladder 40), so that the bladder 40 is snapped over the second end 12 of the connection member 10 while also fixing the earbud body 30 more firmly over the connection member 10.

In this embodiment, in order to increase the fastness of the earbud, the earbud further includes a snap member 50, and the snap member 50 is ring shaped and includes a first snap-fit part 51 and a second snap-fit part 52 which are matched with each other. The first snap-fit part 51 is semi-annular shaped and the second snap-fit part 52 is semi-annular shaped, and the first snap-fit part 51 and the second snap-fit part 52 cooperate to form a ring-shaped configuration. The first snap-fit part 51 is provided with a stud 510 at a surface thereof facing the second snap-fit part 52, and the second snap-fit 52 is correspondingly provided with a recess 520 to accommodate the stud 510. In addition, for better connection of the snap member 50 and the bladder 40, a side wall of the fixed end 42 of the bladder 40 is provided with arcuate grooves 425, the first snap-fit part 51 is provided with a first arcuate strip 515 and the second snap-fit part 52 is provided with a second arcuate strip 525, and each of the first arcuate strip 515 and the second arcuate strip 525 is engaged into one corresponding arcuate groove 425. Further, the number of arcuate grooves 425 is two, and the two arcuate grooves 425 are spaced apart from each other to prevent the snap member 50 from rotating relative to the fixed end 42 of the bladder 40. In other embodiments, the snap member 50 may be an enclosed ring, and more specifically, may be an elastic ring and provided with a protrusion to be engaged into the arcuate groove 425.

Specifically, the first snap-fit part 51 and the second snap-fit part 52 are bonded together by an ultrasonic process. The first snap-fit part 51 is provided with a projection at a surface thereof facing the second snap-fit part 52, the projection 55 is thermally fused to couple with the second snap-fit part 52 during an ultrasonic processing. Referring again to FIGS. 6 and 7, the snap member 50 tightly secures the fixed end 42 of the bladder 40 and a portion of the earbud body 30 proximal to the bladder 40, thereby further securing the bladder 40, the earbud body 30 to the connection member 10.

When assembled, firstly the regulating valve 20 is mounted around the first end 11 of the connection member 10, and then the earbud body 30 is mounted around the regulating valve 20 and the first end 11 of the connection member 10, and then the bladder 40 with the fluid is mounted around the second end 12 of the connection member 10, and finally the snap member 50 is assembled to further fix the regulating valve 20, the earbud body 30 and the bladder 40 on the connection member 10.

Please referring to FIGS. 8-11, which show the state of the earbud of this embodiment in use after inserted into the ear canal, i.e., the state that the bladder 40 is compressed, the fluid flows from the second cavity 41, passes through the through hole 13 and the flow channel 25, and then pushes open the adjustment opening 220 to enter the first cavity 31, so that causes the earbud body 30 to expand. At this point, the bladder 40 has smaller volume than its volume in the natural state; and the earbud body 30 expands under the fluid pressure, so that the outer wall of the earbud body 30 attaches to the ear canal closely.

Referring to FIGS. 12-16, after the earbud is removed from the ear canal by the user, the earbud body 30 is pressed directly and in turn the working end 22 of the regulating valve 20 is squeezed through the earbud body 30, so that two ends of the adjustment opening 220 are close to each other to open the adjustment opening 220, this is an open state.

The opened adjustment opening 220 communicates the first cavity 31 with the flow channel 25, the fluid flows back from the first cavity 31, passes through the adjustment opening 220, the flow channel 25 and the through hole 13 and returns to the bladder 40 until the bladder 40 returns to its natural initial state, the user stops squeezing the earbud body 30 and the regulating valve 20, the earbud body 30 and the regulating valve 20 return to their natural state for the next use.

The earbud of the present application has multiple advantages for its clever structural design:

1. the earbud can be repeatedly cleaned and used;
2. The earbud expands from inside to outside and has better sealing effect;
3. double silicone gel layers of the earbud provide better sound insulation; and
4. The size of the earbud may be adjusted according to the needs (the earbud body 30 may be adjusted from small to large, and when needed, it can be removed to recover to its natural state and then may be readjusted), such that the earbud has strong adaptability, strong fastness and is not easy to fall off.

Figure 17:
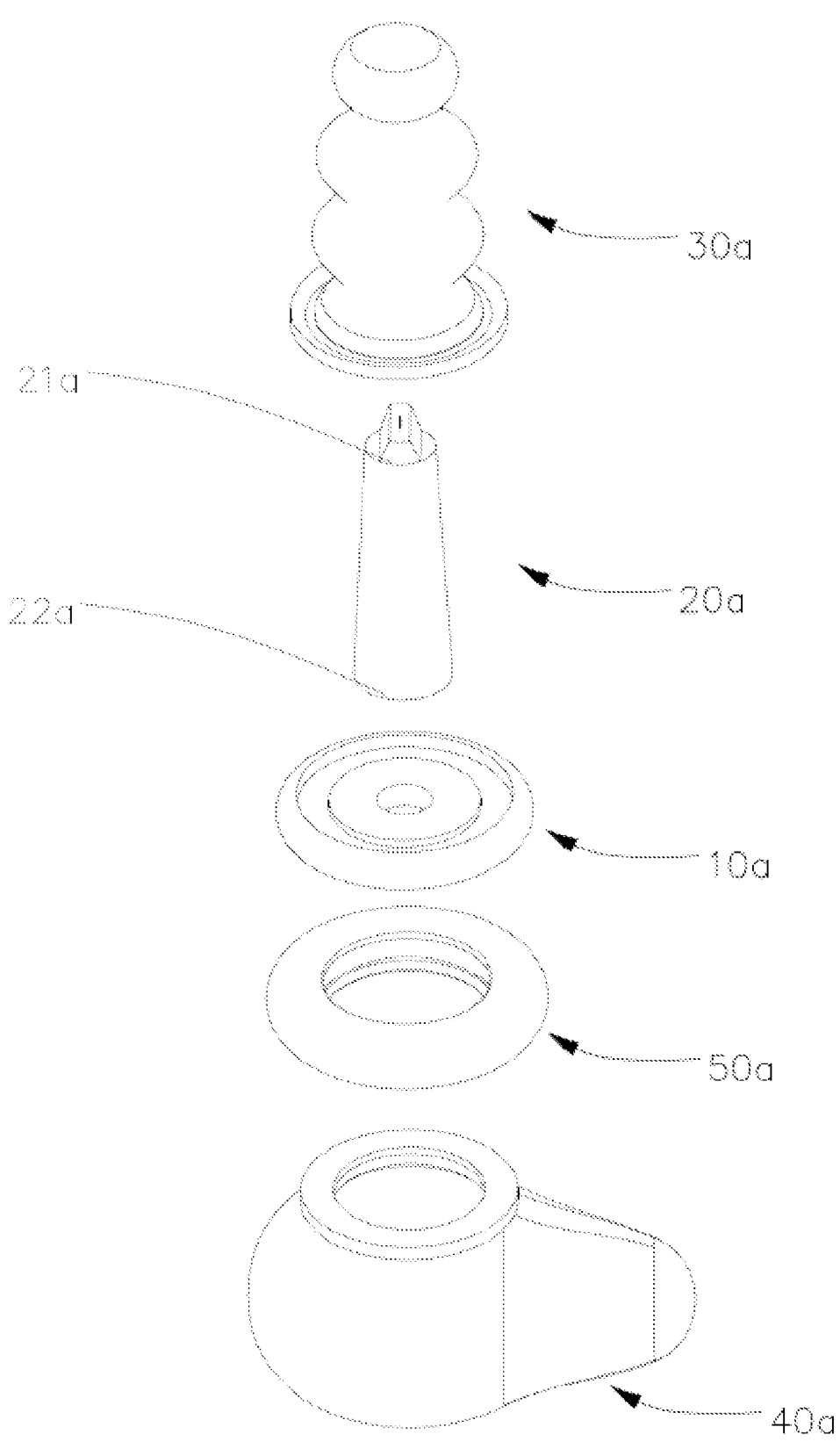
FIG. 17 is a schematic view of an earbud of a second embodiment of the present application.
Figure 18:
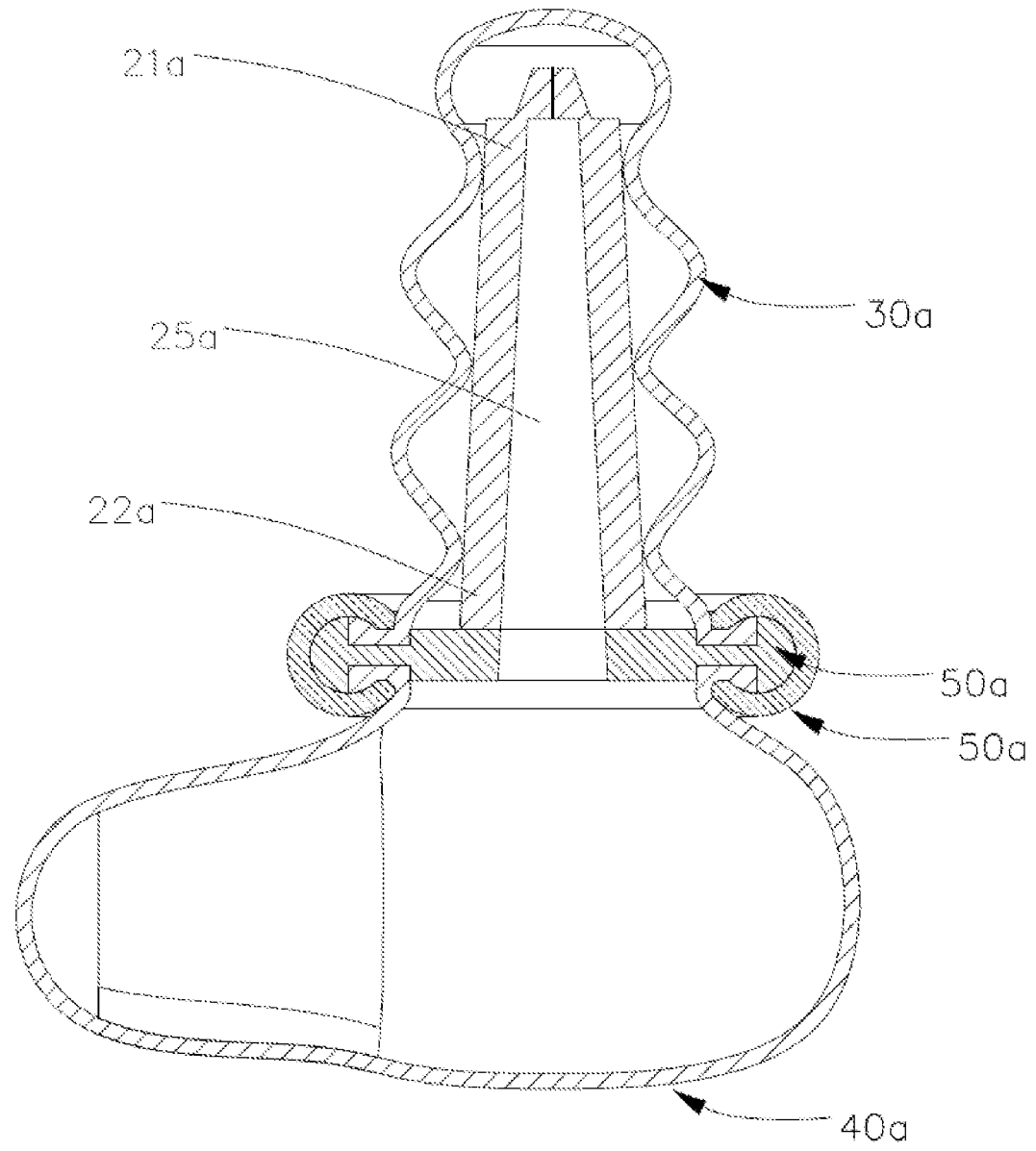
FIG. 18 is a cross-sectional view of the earbud of FIG. 17.

Referring to FIGS. 17-18, a second embodiment of an earbud of the present application is shown. The earbud includes a connection member 10a, a regulating valve 20a, an earbud body 30a, a bladder 40a, and a snap 50a. The regulating valve 20a includes a connection end 21a and a working end 22a, and defines a flow channel 25a therein. The difference between this earbud and the ear bud earbud of the first embodiment is mainly in shapes. The regulating valve 20a is tightly connected to an end face of the connection member 10a by means of over-molding. In addition, the regulating valve 20a is cylindrical-shaped. The regulating valve 20a gradually decreases in cross-sectional dimension from the connection end 21a to the working end 22a, and the flow channel 25a gradually decreases in cross-sectional dimension from the connection end 21a to the working end 22a. The snap member 50a fixes the earbud body 30a and bladder 40a to the connection member 10a, respectively. The snap 50a is ring shaped and has a cross-section being generally C-shaped, and an opening of the C-shape is arranged inwardly.

The embodiments set forth above express only a few embodiments of the present application, and the description is specific and detailed, but is not to be construed as limiting the scope of the application. It should be noted that, for ordinary skill in the art, a number of variations and modifications can be made without departing from the inventive concept, and are within the protection scope of the present application. Therefore, the protection scope of the present application should be subject to the appended claims.

What is claimed is:

1. An earbud, comprising:
   a connection member comprising opposite first end and second end and defining a through hole therein, the though hole extending through the first end and the second end;
   a regulating valve defining a flow channel therein and comprising a connection end and a working end, the connection end tightly connected to the connection member, the working end defining a flat adjustment opening, the flow channel communicating with the through hole of the connection member;
   an earbud body mounted around the regulating valve and connected tightly to the connection member or the regulating valve, the earbud body defining a first cavity therein; and a bladder tightly connected to the connection member and defining a second cavity for containing fluid therein, the second cavity in communication with the through hole of the connection member;

when the earbud is in a natural state, the flat adjustment opening is in a closed state to prevent the first cavity from communicating with the flow channel;

when the bladder is compressed, the fluid flows from the second cavity, passes through the through hole and the flow channel, pushes open the flat adjustment opening and enters the first cavity to make the earbud body expand;

when the fluid stops to enter the first cavity via the flat adjustment opening, the flat adjustment opening reverts to the closed state to prevent backflow of the fluid from the first cavity into the flow channel; and when the working end of the regulating valve is compressed to open the flat adjustment opening, the fluid flows back from the first cavity, passes through the flat adjustment opening, the flow channel and the through hole and returns to the bladder, so as to make the earbud body to contract to its natural state.

2. The earbud as claimed in claim 1, wherein the connection end of the regulating valve is tightly connected to the first end of the connection member; and the bladder is tightly connected to the second end of the connection member.

3. The earbud as claimed in claim 2, wherein the connection member further comprises a main rod, the first end and the second end are provided at two ends of the main rod, respectively; and a size of each of the first end and second end is larger than the size of the main rod.

4. The earbud as claimed in claim 3, wherein each of the main rod, the first end and the second end is cylindrical-shaped, and a diameter of each of the first end and the second end is larger than the diameter of the main rod.

5. The earbud as claimed in claim 1, wherein the regulating valve is an elastic gel member, the flow channel of the regulating valve forms a connection hole at the connection end; and the size of the connection hole in the natural state is smaller than the size of the first end.

6. The earbud as claimed in claim 1, wherein an end surface of the working end is elongated, and the flat adjustment opening is provided on the end surface of the working end and is elongated and linear-shaped in the natural state.

7. The earbud as claimed in claim 6, wherein an outer side of the working end is provided with inclined pressure surfaces at positions corresponding to two sides of the flat adjustment opening.

8. The earbud as claimed in claim 1, wherein the earbud body is an elastic gel member.

9. The earbud as claimed in claim 8, wherein an end of the earbud body facing the regulating valve defines a mounting opening, a size of the mounting opening in the natural state is smaller than the size of the regulating valve, and the earbud body is tightly mounted around the entire regulating valve and the first end of the connecting member after expanding of the mounting opening.

10. The earbud as claimed in claim 1, wherein the bladder is an elastic gel member and is connected to the second end by snap-fit.

11. The earbud as claimed in claim 10, wherein the connection member further comprises a main rod connecting the first end with the second end, the earbud body is tightly mounted around the main rod, and the bladder is mounted around a portion of the earbud body mounted around the main rod.

12. The earbud as claimed in claim 1, further comprising a snap member mounted around the earbud body and the bladder, the snap member is configured for fixing the regulating valve, the earbud body and the bladder to the connection member.

13. The earbud as claimed in claim 12, wherein the bladder is provided with a fixed end facing the connection member, a side wall of the fixed end defines an arcuate groove; and the snap member is provided with a protrusion that is engaged into the arcuate groove.

14. The earbud as claimed in claim 12, wherein the snap member comprises a first snap-fit part and a second snap-fit part which are matched with each other, the first snap-fit part is semi-annular-shaped and the second snap-fit part is semi-annular-shaped, and the first snap-fit part and the second snap-fit part cooperate to form a ring-shaped configuration.

15. The earbud as claimed in claim 14, wherein the first snap-fit part is provided with a stud at a surface thereof facing the second snap-fit part, and the second snap-fit is correspondingly provided with a recess to accommodate the stud.

16. An earbud, comprising:

an earbud body configured for inserting into an ear canal, the earbud body defining a first cavity therein;

a bladder defining a second cavity for accommodating fluid therein; and a regulating valve comprising a connection end and an elastic working end, the connection end communicating with the second cavity of the bladder, the elastic working end defining an adjustment opening facing towards the first cavity of the earbud body;

when the earbud is in the natural state, the adjustment opening is closed to disconnect the first cavity from the second cavity;

when the bladder is compressed to open the adjustment opening, the fluid flows from the second cavity to the first cavity via the adjustment opening, so that the earbud body expands to attach to the ear canal; and when the earbud body is compressed to open the adjustment opening, the fluid flows back from the first cavity to the second cavity via the adjustment opening, so that the earbud body recovers to its natural state;

wherein a hollow connection member is arranged between the bladder and the regulating valve, one end of the hollow connection member is connected to the bladder and communicates with the second cavity, the other end of the hollow connection member is connected to and communicates with the connection end of the regulating valve, and the elastic working end extends into the first cavity of the earbud body; and wherein the earbud body is mounted around the regulating valve and has an open end connected to the other end of the hollow connection member, the bladder comprises an open end connected to the one end of the hollow connection member, and a snap member is mounted around the open ends of the earbud body and bladder for fixing the earbud body and bladder together.

17. The earbud as claimed in claim 16, wherein at least a portion of the regulating valve adjacent to the elastic working end has a cross section gradually decreasing towards the elastic working end.

18. The earbud as claimed in claim 16, wherein the adjustment opening is elongated and linear-shaped in the closed state.

* * * * *